US011865163B2

(12) United States Patent
Brimijoin et al.

(10) Patent No.: US 11,865,163 B2
(45) Date of Patent: Jan. 9, 2024

(54) METHODS AND MATERIALS FOR USING BUTYRYLCHOLINESTERASES TO TREAT CANCER

(71) Applicant: Mayo Foundation for Medical Education and Research, Rochester, MN (US)

(72) Inventors: William S. Brimijoin, Rochester, MN (US); Liewei Wang, Rochester, MN (US); Yang Gao, Rochester, MN (US); Ping Chen, Rochester, MN (US); Liyi Geng, Rochester, MN (US); Jia Yu, Rochester, MN (US); Judy C. Boughey, Rochester, MN (US); Matthew P. Goetz, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 940 days.

(21) Appl. No.: 16/333,835

(22) PCT Filed: Sep. 15, 2017

(86) PCT No.: PCT/US2017/051694
§ 371 (c)(1),
(2) Date: Mar. 15, 2019

(87) PCT Pub. No.: WO2018/053216
PCT Pub. Date: Mar. 22, 2018

(65) Prior Publication Data
US 2019/0255154 A1    Aug. 22, 2019

Related U.S. Application Data

(60) Provisional application No. 62/394,939, filed on Sep. 15, 2016.

(51) Int. Cl.
*A61K 38/46* (2006.01)
*A61P 35/00* (2006.01)
*C12N 15/86* (2006.01)
*C12N 9/18* (2006.01)

(52) U.S. Cl.
CPC ............ *A61K 38/465* (2013.01); *A61P 35/00* (2018.01); *C12N 9/18* (2013.01); *C12N 15/86* (2013.01); *A01K 2207/12* (2013.01); *A01K 2227/105* (2013.01); *A01K 2267/0331* (2013.01); *C12N 2710/10043* (2013.01); *C12N 2750/14143* (2013.01); *C12Y 301/01008* (2013.01)

(58) Field of Classification Search
None
See application file for complete search history.

(56) References Cited

U.S. PATENT DOCUMENTS

| 5,580,859 A | 12/1996 | Felgner et al. |
| 5,589,466 A | 12/1996 | Felgner et al. |
| 6,001,625 A | 12/1999 | Broomfield et al. |
| 8,399,644 B1 | 3/2013 | Zhan et al. |
| 2004/0086976 A1 | 5/2004 | Fleer et al. |
| 2004/0121970 A1 | 6/2004 | Watkins et al. |
| 2008/0213281 A1 | 9/2008 | Watkins et al. |
| 2010/0254994 A1 | 10/2010 | Raso |
| 2011/0160121 A1 | 6/2011 | Brizzi et al. |
| 2013/0071394 A1 | 3/2013 | Troyer et al. |
| 2014/0294926 A1 | 10/2014 | Chang et al. |
| 2014/0378380 A1 | 12/2014 | Brizzi et al. |
| 2016/0032005 A1 | 2/2016 | Borg et al. |
| 2017/0051261 A1 | 2/2017 | Geng et al. |

FOREIGN PATENT DOCUMENTS

WO    WO 2002/064796    8/2002

OTHER PUBLICATIONS

US 6,884,780 B2, 04/2005, Drummond et al. (withdrawn)
NCBI Blast search M16541. Datasheet [online]. Search for the sequence deposited under GenBank accession #M16541. Retrieved on Apr. 4, 2022. Downloaded from the internet: <https://blast.ncbi.nlm.nih.gov/Blast.cgi> pp. 1-2.*
NCBI Blast comparison. Datasheet [online]. Compare amino acid sequence of translated M16541 with instantly claimed SEQ ID No. 3. Retrieved on Apr. 4, 2022. Downloaded from the internet: <https://blast.ncbi.nlm.nih.gov/Blast.cgi> pp. 1-2.*
Nakai, K. et al. Aug. 2016. 15. A perspective on anti-EGFR therapies targeting triple-negative breast cancer. American Journal of Cancer Research 6(8): 1609-1623; specif. p. 1609.*
Chen, V.P. et al. Feb. 2015. Plasma butyrylcholinesterase regulates ghrelin to control aggression. Proceedings of the National Academy of Sciences (PNAS) 112(7): 2251-2256; specif. pp. 2251, 2252, 2253, 2254.*
Jeffery, P.L. et al. 2005. Expression and function of the ghrelin axis, including a novel preproghrelin isoform, in human breast cancer tissues and cell lines. Endocrine-Related Cancer 12: 839-850; specif. pp. 839, 840, 844.*
Kojima, M. et al. 2005. Ghrelin: structure and function. Physiological Reviews 85: 495-522; specif. pp. 508, 509, 511.*

(Continued)

*Primary Examiner* — Michael Barker
*Assistant Examiner* — Sharon M. Papciak
(74) *Attorney, Agent, or Firm* — Fish & Richardson P.C.

(57) ABSTRACT

This document provides methods and materials for using butyrylcholinesterases (BChE) to treat cancer (e.g., triple negative breast cancer or prostate cancer). For example, methods and materials for using nucleic acid vectors (e.g., viral vectors) to express BChE polypeptides under conditions that reduce the number of cancer cells (e.g., triple negative breast cancer cells or prostate cancer cells) within a mammal (e.g., a human) and/or reduce the growth rate of cancer cells (e.g., triple negative breast cancer cells or prostate cancer cells) within a mammal (e.g., a human) are provided.

11 Claims, 4 Drawing Sheets

Specification includes a Sequence Listing.

(56) References Cited

OTHER PUBLICATIONS

Battisti et al., "Cholinesterase activities and biochemical determinations in patients with prostate cancer: influence of Gleason score, treatment and bone metastasis," Biomed. Pharmacother., 66(4):249-55, Jun. 2012.
Boberg et al., "Copy number variation in ACHE/EPHB4 (7q22) and in BCHE/MME (3q26) genes in sporadic breast cancer," Chem. Biol. Interact., 203(1):344-7, 2013.
Boberg et al., "Molecular forms of butyrylcholinesterase and obesity," Genet Mol Biol., 33(3):452-4, 2010.
Bryan et al., http://www.elsevierblogs.conn/currentconnnnents/?p=962, Implications of protein fold switching, p. 1-4, 2013.
Carlson and Cummings, "Prospects for an anti-ghrelin vaccine to treat obesity," Mol. Interv., 6:249-52, 2006.
Cataliotti et al., "Oral Brain Natriuretic Peptide: A Novel Strategy for Chronic Protein Therapy for Cardiovascular Disease," Trends Cardiovasc. Med., 17(1):10-4, Jan. 2007.
Chen et al., "Plasma butyrylcholinesterase regulates ghrelin to control aggression," Proc. Natl. Acad. Sci. USA, 112(7):2251-6, Feb. 2015.
Dantas et al., "Obesity and variants of the GHRL (ghrelin) and BCHE (butyrylcholinesterase) genes," (Translated from English) Genet. Mol. Biol., 34(2):205-7, 2011.
De Vriese and Delporte, "Ghrelin: a new peptide regulating growth hormone release and food intake," Internatl. J. Biochem. Cell Biol., 40(8):1420-4, 2008.
De Vriese et al., "Ghrelin degradation by serum and tissue homogenates: identification of the cleavage sites," Endocrinology., 145(11):4997-5005, 2004.
De Vriese et al., "Influence of ghrelin on food intake and energy homeostasis," Curr. Opin. Clin. Nutr. Metab. Care, 10:615-9, 2007.
Delhanty et al., "Ghrelin: the differences between acyl- and des-acyl ghrelin," Eur. J. Endocrinol., 167(5):601-8, 2012.
Delporte, "Structure and physiological actions of Ghrelin," Scienti Hindawi Publish. Corp., 2013:518909, 2013.
Duysen et al., "The butyrylcholinesterase knockout mouse a research tool in the study of drug sensitivity, bio-distribution, obesity and Alzheimer's disease," Expert Opin. Drug Metab. Toxicol., 5(5):523-8, 2009.
Garry, "Serum Cholinesterase Variants: Examination of Several Differential Inhibitors, Salts, and Buffers Used to Measure Enzyme Activity," Clin. Chem., 17(3):183-91, Mar. 1971.
GenBank Accesion No. AAY59235.1, "Conserved hypothetical protein [Burkholderia mallei ATCC 23344]," 2 pages, Jan. 31, 2014.
GenBank Accesion No. ADR01048.1, "Maturase K, partial (chloroplast) [Parthenium hysterophorus]," 1 page, Jan. 11, 2011.
Geng et al., "Gene Transfer of Mutant Mouse Cholinesterase Provides High Lifetime Expression and Reduced Cocaine Responses with No Evident Toxicity," PLoS One., 8(6):e67446, 2013.
Guatelli et al., "Isothermal, in vitro amplification of nucleic acids by a multienzyme reaction modeled after retroviral replication," Proc. Natl. Acad. Sci. USA, 87(5):1874-8, Mar. 1990.
Kim et al., "Lifetime correction of genetic deficiency in mice with a single injection of helper-dependent adenoviral vector," Proc. Natl. Acad. Sci. USA, 98(23):13282-7, Nov. 2001.
Kojima and Kangawa., "Ghrelin: Structure and Function," Physiol. Rev., 85(2):495-522, 2005.
Kumar et al., "Serum butyrylcholineslerase and zinc in breast cancer," J. Cancer Res. Ther., 13(2):367-70, Apr. 2017.
Lewis, "PCR's Competitors are Alive and Well and Moving Rapidly Towards Commercialization," Genetic Engineering News, 12(9):1, 1992.
Li et al., The butyrylcholinesterase knockout mouse is obese on a high-fat diet. (Translated from eng) Chem. Biol. Interact., 175(1-3):88-91, 2008.
Maqbool et al., "The substrate-binding protein in bacterial ABC transporters: dissecting roles in the evolution of substrate specificity," Biochem. Soc. Trans., 43(5):1011-7, 2015.
Miller et al., "Amphiphilic Conjugates of Human Brain Natriuretic Peptide Designed for Oral Delivery: In Vitro Activity Screening," Bioconjugate Chem., 17(2):267-74, Feb. 2006.
Parks et al., "A helper-dependent adenovirus vector system: Removal of helper virus by Cre-mediated excision of the viral packaging signal," Proc. Natl. Acad. Sci. USA., 93:13565-70, Nov. 1996.
PCT International Preliminary Report on Patentability in International Appln. No. PCT/US2017/051694 dated Mar. 28, 2019, 8 pages.
PCT International Search Report and Written Opinion in International Appln. No. PCT US2017/051694 dated Nov. 28, 2017, 11 pages.
Renee et al., "Tetramerization domain of human butyrylcholinesterase is at the C-terminus," Biochem. J., 327(3):747-57, Nov. 1997.
Santarpia et al., "Butyrylcholineslerase as a prognostic marker: a review of the literature," J. Cachexia Sarcopenia Muscle.,4(1):31-9, 2013.
Satou et al., "Identification and Characterization of Acyl-Protein Thioesterase 1/Lysophospholipase I as a Ghrelin Deacylation/ Lysophospholipid Hydrolyzing Enzyme in Fetal Bovine Serum and Conditioned Medium," Endocrinology, 151(10):4765-75, Oct. 2010.
Schwandt et al., "Differential Roles for Octanoylated and Decanoylated Ghrelins in Regulating Appetite and Metabolism," Internatl., J. Peptides, 2010:1-7, 2010.
Tinoco et al. "Ghrelin Increases Food Intake, Swimming Activity and Growth in Juvenile Brown Trout (*Salmo trutta*)," Physiol. Behav., 124:15-22,Oct. 2013.
Tschop et al., "Ghrelin induces adiposity in rodents," Nature, 407(6806):908-13, Oct. 2000.
Veronese and Mero, "The Impact of PEGylation on Biological Therapies," BioDrugs, 22(5):315-29, Sep. 2008.
Veronese and Pasut, "PEGylation, successful approach to drug delivery," Drug Discov. Today, 10(21):1451-8, Nov. 2005.
Wang et al., "Albubnp, a Recombinant B-type Natriuretic Peptide and Human Serum Albumin Fusion Hormone, as a Long-Term Therapy of Congestive Heart Failure," Pharm. Res., 21(11):2105-11, Nov. 2004.
Weiss, "Hot prospect for new gene amplifier," Science, 254(5036):1292-3, Nov. 1991.
Thomas et al., "Rethink of EGFR in Cancer With Its Kinase Independent Function on Board," Front. Oncology, Aug. 2019, 9:800, 16 pages.

* cited by examiner

FIG. 1 mouse BChE amino acid sequence (with 29aa signal peptide at N-terminus):
METQHTKVTQTHFLLWILLLCMPFGKSHTEEDFIITTKTGRVRGLSMPVLGGTVTAFLGIPYA
QPPLGSLRFKKPQPLNKWPDIHNATQYANSCYQNIDQAFPGFQGSEMWNPNTNLSEDCLYLNV
WIPVPKPKNATVMVWIYGGGFQTGTSSLPVYDGKFLARVERVIVVSMNYRVGALGFLAFPGNP
DAPGNMGLFDQQLALQWVQRNIAAFGGNPKSITIFGESAGAASVSLHLLCPQSYPLFTRAILESGS
SNAPWAVKHPEEARNRTLTLAKFTGCSKENEMEMIKCLRSKDPQEILRNERFVLPSDSILSINFGP
TVDGDFLTDMPHTLLQLGKVKKAQILVGVNKDEGTAFLVYGAPGFSKDNDSLITRKEFQEGLN
MYFPGVSRLGKEAVLFYYVDWLGEQSPEVYRDALDDVIGDYNIICPALEFTKKFAELENNAFFY
FFEHRSSKLPWPEWMGVMHGYEIEFVFGLPLGRRVNYTRAEEIFSRSIMKTWANFAKYGHPNGT
QGNSTMWPVFTSTEQKYLTLNTEKSKIYSKLRAPQCQFWRLFFPKVLEMTGDIDETEQEWKAGF
HRWSNYMMDWQNQFNDYTSKKESCTAL (SEQ ID NO:1)

mouse BChE coding sequence:
ATGGAGACTCAGCATACCAAGGTAACACAGACCCACTTCCTCCTATGGATTCTTCTGCTCTG
CATGCCTTTTGGGAAGTCACACACTGAAGAAGACTTCATAATTACAACCAAGACCGGAAGG
GTCCGAGGGCTGAGCATGCCAGTTCTTGGTGGCACGGTGACTGCCTTTCTCGGTATCCCCTAT
GCACAACCTCCTCTGGGTAGCCTAAGATTCAAAAAGCCGCAACCCTTAAACAAATGGCCTGA
CATCCATAATGCCACTCAATATGCAAATTCTTGTTATCAGAACATAGACCAAGCCTTCCCAG
GCTTCCAGGGGTCAGAAATGTGGAATCCAAACACAAACCTCAGTGAAGACTGCTTGTATCTG
AATGTTTGGATTCCAGTACCGAAGCCTAAAAATGCCACTGTCATGGTATGGATCTATGGTGG
TGGCTTTCAAACTGGGACCTCTTCTCTACCTGTTTACGATGGGAAGTTTCTAGCTCGTGTTGA
AAGAGTTATTGTAGTTTCGATGAACTATAGGGTAGGTGCTCTAGGATTCCTAGCTTTTCCCGG
AAATCCCGATGCTCCAGGAAACATGGGTTTATTTGATCAACAGTTGGCACTTCAATGGGTCC
AAAGAAATATAGCTGCTTTTGGAGGGAATCCTAAAAGTATAACGATTTTTGGAGAAAGTGC
AGGGGCAGCTTCAGTTAGCTTACATTTGCTCTGCCCCCAAAGTTATCCTTTGTTTACCAGAGC
CATTCTTGAAAGTGGCTCCTCTAATGCCCCCTGGGCAGTAAAGCATCCTGAGGAAGCCAGAA
ACAGAACCTTGACCTTAGCTAAATTTACTGGTTGCTCAAAGGAAAATGAGATGGAGATGATT
AAATGCCTTCGAAGTAAAGATCCTCAGGAAATTCTTCGCAATGAAAGGTTCGTTCTCCCTC
TGATTCCATCTTATCCATAAATTTTGGTCCAACAGTGGATGGCGATTTTCTCACCGATATGCC
CCACACACTACTCCAACTAGGAAAAGTGAAAAAAGCTCAGATCTTAGTGGGAGTTAACAAA
GATGAAGGGACAGCTTTCCTAGTGTACGGTGCTCCGGGTTTCAGCAAAGACAATGATAGCCT
TATCACAAGGAAGGAATTTCAAGAAGGTTTAAATATGTATTTCCCTGGAGTGAGCAGATTGG
GCAAGGAAGCAGTTCTTTTCTACTACGTGGACTGGTTAGGTGAGCAGTCACCAGAAGTCTAC
CGTGACGCTTTGGATGATGTTATTGGAGATTACAACATCATCTGCCCTGCACTGGAGTTTACC
AAGAAATTTGCAGAGCTTGAAAACAATGCTTTTTTCTACTTTTTCGAACATCGCTCTTCCAAA
CTACCTTGGCCGGAATGGATGGGAGTGATGCATGGCTATGAAATTGAATTTGTGTTTGGCTT
ACCTCTGGGAAGAAGAGTTAATTATACGAGAGCTGAGGAAATCTTTAGTCGATCCATAATGA
AAACTTGGGCAAATTTTGCAAAATATGGTCACCCCAATGGGACCCAGGGCAATAGCACAAT
GTGGCCTGTCTTCACAAGTACTGAACAAAAATACCTAACATTGAACACAGAGAAGTCAAAA
ATATACTCTAAACTTCGTGCTCCCCAATGTCAGTTCTGGAGACTATTTTTTCCAAAAGTCTTG
GAAATGACAGGAGATATTGATGAAACGGAGCAAGAGTGGAAGGCAGGATTTCATCGCTGGA
GCAATTACATGATGGACTGGCAAAATCAATTTAACGATTACACTAGCAAGAAAGAGAGCTG
TACAGCTCTCTAA (SEQ ID NO:2)

FIG. 2 human BChE amino acid sequence (with 28aa signal peptide at N-terminus):
MHSKVTIICIRFLFWFLLLCMLIGKSHTEDDIIIATKNGKVRGMNLTVFGGTVTAFLGIPYAQPP
LGRLRFKKPQSLTKWSDIWNATKYANSCCQNIDQSFPGFHGSEMWNPNTDLSEDCLYLNVWIPA
PKPKNATVLIWIYGGGFQTGTSSLHVYDGKFLARVERVIVVSMNYRVGALGFLALPGNPEAPGN
MGLFDQQLALQWVQKNIAAFGGNPKSVTLFGESAGAASVSLHLLSPGSHSLFTRAILQSGSFNAP
WAVTSLYEARNRTLNLAKLTGCSRENETEIIKCLRNKDPQEILLNEAFVVPYGTPLSVNFGPTVD
GDFLTDMPDILLELGQFKKTQILVGVNKDEGTAFLVYGAPGFSKDNNSIITRKEFQEGLKIFFPGV
SEFGKESILFHYTDWVDDQRPENYREALGDVVGDYNFICPALEFTKKFSEWGNNAFFYYFEHRS
SKLPWPEWMGVMHGYEIEFVFGLPLERRDNYTKAEEILSRSIVKRWANFAKYGNPNETQNNSTS
WPVFKSTEQKYLTLNTESTRIMTKLRAQQCRFWTSFFPKVLEMTGNIDEAEWEWKAGFHRWNN
YMMDWKNQFNDYTSKKESCVGL (SEQ ID NO:3)

human BChE coding sequence:
ATGCATAGCAAAGTCACAATCATATGCATCAGATTTCTCTTTTGGTTTCTTTTGCTCTGCATG
CTTATTGGGAAGTCACATACTGAAGATGACATCATAATTGCAACAAAGAATGGAAAAGTCA
GAGGGATGAACTTGACAGTTTTTGGTGGCACGGTAACAGCCTTTCTTGGAATTCCCTATGCA
CAGCCACCTCTTGGTAGACTTCGATTCAAAAAGCCACAGTCTCTGACCAAGTGGTCTGATAT
TTGGAATGCCACAAAATATGCAAATTCTTGCTGTCAGAACATAGATCAAAGTTTTCCAGGCT
TCCATGGATCAGAGATGTGGAACCCAAACACTGACCTCAGTGAAGACTGTTTATATCTAAAT
GTATGGATTCCAGCACCTAAACCAAAAAATGCCACTGTATTGATATGGATTTATGGTGGTGG
TTTTCAAACTGGAACATCATCTTTACATGTTTATGATGGCAAGTTTCTGGCTCGGGTTGAAAG
AGTTATTGTAGTGTCAATGAACTATAGGGTGGGTGCCCTAGGATTCTTAGCTTTGCCAGGAA
ATCCTGAGGCTCCAGGGAACATGGGTTTATTTGATCAACAGTTGGCTCTTCAGTGGGTTCAA
AAAAATATAGCAGCCTTTGGTGGAAATCCTAAAAGTGTAACTCTCTTTGGAGAAAGTGCAGG
AGCAGCTTCAGTTAGCCTGCATTTGCTTTCTCCTGGAAGCCATTCATTGTTCACCAGAGCCAT
TCTGCAAAGTGGATCCTTTAATGCTCCTTGGGCGGTAACATCTCTTTATGAAGCTAGGAACA
GAACGTTGAACTTAGCTAAATTGACTGGTTGCTCTAGAGAGAATGAGACTGAAATAATCAA
GTGTCTTAGAAATAAAGATCCCCAAGAAATTCTTCTGAATGAAGCATTTGTTGTCCCTATG
GGACTCCTTTGTCAGTAAACTTTGGTCCGACCGTGGATGGTGATTTTCTCACTGACATGCCAG
ACATATTACTTGAACTTGGACAATTTAAAAAAACCCAGATTTTGGTGGGTGTTAATAAAGAT
GAAGGGACAGCTTTTTTAGTCTATGGTGCTCCTGGCTTCAGCAAAGATAACAATAGTATCAT
AACTAGAAAAGAATTTCAGGAAGGTTTAAAAATATTTTTTCCAGGAGTGAGTGAGTTTGGAA
AGGAATCCATCCTTTTTCATTACACAGACTGGGTAGATGATCAGAGACCTGAAAACTACCGT
GAGGCCTTGGGTGATGTTGTTGGGGATTATAATTTCATATGCCCTGCCTTGGAGTTCACCAA
GAAGTTCTCAGAATGGGGAAATAATGCCTTTTTCTACTATTTTGAACACCGATCCTCCAAACT
TCCGTGGCCAGAATGGATGGGAGTGATGCATGGCTATGAAATTGAATTTGTCTTTGGTTTAC
CTCTGGAAAGAAGAGATAATTACACAAAAGCCGAGGAAATTTTGAGTAGATCCATAGTGAA
ACGGTGGGCAAATTTTGCAAAATATGGGAATCCAAATGAGACTCAGAACAATAGCACAAGC
TGGCCTGTCTTCAAAAGCACTGAACAAAAATATCTAACCTTGAATACAGAGTCAACAAGAAT
AATGACGAAACTACGTGCTCAACAATGTCGATTCTGGACATCATTTTTTCCAAAAGTCTTGG
AAATGACAGGAAATATTGATGAAGCAGAATGGGAGTGGAAAGCAGGATTCCATCGCTGGAA
CAATTACATGATGGACTGGAAAAATCAATTTAACGATTACACTAGCAAGAAAGAAAGTTGT
GTGGGTCTCTAA (SEQ ID NO:4)

METHODS AND MATERIALS FOR USING BUTYRYLCHOLINESTERASES TO TREAT CANCER

CROSS-REFERENCE TO RELATED APPLICATIONS

This application is a National Stage application under 35 U.S.C. § 371 of International Application No. PCT/US2017/051694, having an International Filing Date of Sep. 15, 2017, which claims priority to U.S. Application Ser. No. 62/394,939, filed on Sep. 15, 2016. The disclosure of the prior application is considered part of the disclosure of this application, and is incorporated in its entirety into this application.

BACKGROUND

1. Technical Field

This document relates to methods and materials for using butyrylcholinesterases (BChE) to treat cancer (e.g., triple negative breast cancer or prostate cancer). For example, this document provides methods and materials for using nucleic acid vectors (e.g., viral vectors) to express BChE polypeptides under conditions that reduce the number of cancer cells (e.g., triple negative breast cancer cells or prostate cancer cells) within a mammal (e.g., a human) and/or reduce the growth rate of cancer cells (e.g., triple negative breast cancer cells or prostate cancer cells) within a mammal (e.g., a human).

2. Background Information

Cancer is the second-leading cause of death in the United States. One example of cancer is breast cancer, which develops from breast tissue and is the most common invasive cancer in women. Breast cancer is usually treated with surgery, which may be followed by chemotherapy or radiation therapy, or both chemotherapy and radiation therapy. One type of breast cancer is referred to as triple negative breast cancer, which means that the cancer cells do not express the genes for estrogen receptor (ER), progesterone receptor (PR), or Her2/neu (as known as ErbB2 or CD340). Another type of cancer that is a major cause of death in men is prostate cancer.

SUMMARY

This document provides methods and materials for using nucleic acid vectors designed to express BChE polypeptides to treat cancer (e.g., triple negative breast cancer or prostate cancer). For example, nucleic acid vectors (e.g., viral vectors) can be designed to express BChE polypeptides and administered to a mammal (e.g., a human) having cancer (e.g., triple negative breast cancer or prostate cancer) to reduce the number of cancer cells (e.g., triple negative breast cancer cells or prostate cancer cells) within the mammal and/or reduce the growth rate of cancer cells (e.g., triple negative breast cancer cells or prostate cancer cells) within the mammal.

As described herein, a nucleic acid encoding a BChE polypeptide having the ability to hydrolyze acyl ghrelin can be administered to a mammal having cancer cells under conditions wherein the growth rate of cancer cells within the mammal is reduced.

In general, one aspect of this document features a method for treating cancer within a mammal. The method comprises, or consists essentially of, administering a BChE polypeptide or a nucleic acid encoding the polypeptide to the mammal under conditions wherein the number of cancer cells within the mammal is reduced or the growth rate of the cancer within the mammal is reduced. The mammal can be a human. The cancer can be breast cancer. The breast cancer can be triple negative breast cancer. The cancer can be prostate cancer. The method can comprise administering the BChE polypeptide to the mammal. The method can comprise administering the nucleic acid to the mammal. The nucleic acid can be administered to the mammal as a viral vector. The viral vector can be an adenoviral or adeno-associated viral vector. The BChE polypeptide can be a human BChE polypeptide. The BChE polypeptide can comprise the amino acid sequence set forth in SEQ ID NO:3. The BChE polypeptide can comprise the amino acid sequence set forth in SEQ ID NO:3 with a F329M substitution or with a combination with one or more of the following amino acid substitutions: A199S, F227A, S287G A328W, F329M, or Y332G.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 is a sequence listing of a wild-type mouse butyrylcholinesterase (SEQ ID NO:1) along with a nucleic acid sequence (SEQ ID NO:2) that encodes this wild-type mouse butyrylcholinesterase.

FIG. 2 is a sequence listing of a wild-type human butyrylcholinesterase (SEQ ID NO:3) along with a nucleic acid sequence (SEQ ID NO:4) that encodes this wild-type human butyrylcholinesterase.

DETAILED DESCRIPTION

Figure 3:
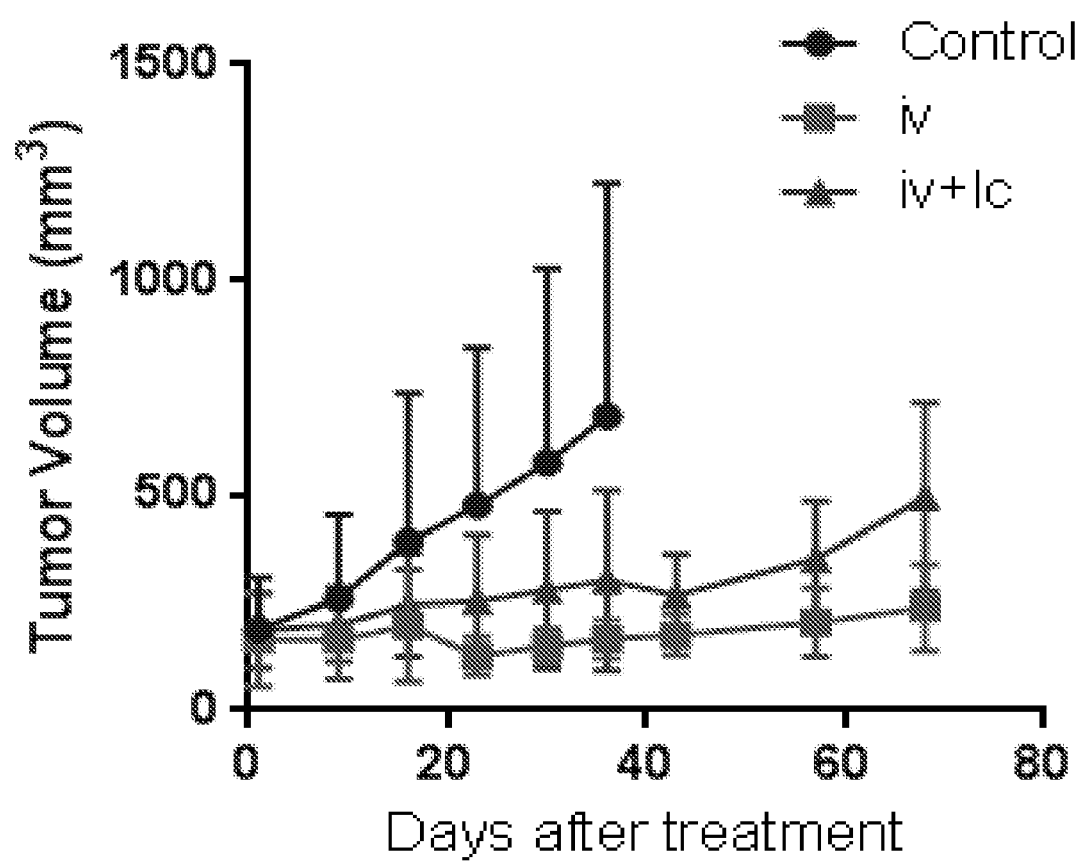
FIG. 3 is a graph plotting tumor volume at the indicated days after treatment with (a) a control vector expressing luciferase injected into the tail vein (control), (b) a vector expressing BChE injected into the tail vein (iv; intravenous injection), or into the tumor (ic; local), or into both the tail vein and the implanted tumor (iv+ic).

This document provides methods and materials for using BChE polypeptides to treat cancer. For example, this document provides nucleic acid vectors (e.g., viral vectors) that contain nucleic acid encoding BChE polypeptides for treating cancer (e.g., breast cancer or prostate cancer) as well as methods for using such nucleic acid vectors to treat cancer (e.g., breast cancer or prostate cancer). In some cases, the nucleic acid vectors (e.g., viral vectors) designed to express a BChE polypeptide provided herein can be administered to a mammal having cancer under conditions that reduce the number of cancer cells within the mammal and/or reduce the growth rate of cancer cells within the mammal.

Any type of mammal having cancer can be treated as described herein. For example, humans and other primates such as monkeys having cancer can be treated with a nucleic acid vector (e.g., viral vector) designed to express a BChE polypeptide provided herein to reduce the number of cancer cells within the mammal and/or to reduce the growth rate of cancer cells within the mammal. In some cases, dogs, cats, horses, cows, pigs, sheep, mice, and rats can be treated with a nucleic acid vector (e.g., viral vector) designed to express a BChE polypeptide as described herein.

Any appropriate cancer can be treated as described herein. For example, breast cancer (e.g., triple negative breast cancer), prostate cancer, lung cancer, thyroid cancer, ovarian cancer, testicular cancer, endometrial cancer, renal cancer, colon cancer, colorectal cancer, adrenocortical tumors, and cancers of the digestive tract and endocrine pancreas can be treated with a nucleic acid vector (e.g., viral vector) designed to express a BChE polypeptide as described herein. For example, a human female with breast cancer that is ER negative, PR negative, and Her2/neu negative can be administered a nucleic acid vector (e.g., viral vector) designed to express a BChE polypeptide to reduce the number of breast cancer cells and/or to reduce the growth rate of the breast cancer cells. In some cases, a human male with prostate cancer can be administered a nucleic acid vector (e.g., viral vector) designed to express a BChE polypeptide to reduce the number of prostate cancer cells and/or to reduce the growth rate of the prostate cancer cells.

Any appropriate method can be used to identify a mammal having cancer. For example, imaging techniques and biopsy techniques can be used to identify mammals (e.g., humans) having cancer (e.g., breast cancer or prostate cancer). Any appropriate method can be used to identify the ER negative, PR negative, and Her2/neu negative status of a mammal's breast cancer. For example, immunological techniques such as staining techniques using antibodies can be used to identify mammals (e.g., humans) having ER negative, PR negative, and Her2/neu negative breast cancer.

Once identified as having cancer (e.g., breast cancer or prostate cancer), the mammal can be administered a nucleic acid vector (e.g., viral vector) designed to express a BChE polypeptide. In some cases, a mammal having cancer (e.g., breast cancer or prostate cancer) can be administered a BChE polypeptide to treat cancer.

A nucleic acid vector to be administered to a mammal to treat cancer as described herein can be designed to encode any appropriate BChE polypeptide. In some cases, when using a BChE polypeptide in place of or in addition to a nucleic acid vector (e.g., viral vector) designed to express a BChE polypeptide, any appropriate BChE polypeptide can be used. For example, a BChE polypeptide, whether administered as a polypeptide or delivered using a nucleic acid vector designed to express the BChE polypeptide, can be designed to include the amino acid sequence set forth in SEQ ID NO:1 or 3 or the amino acid sequence set forth in SEQ ID NO:1 or 3 with the exception that it contains one, two, three, four, five, or more amino acid additions, subtractions, or substitutions. For example, a BChE polypeptide provided herein can have the amino acid sequence set forth in SEQ ID NO:3 with the following six changes: A199S, F227A, S287G A328W, F329M, and Y332G In some cases, a BChE polypeptide provided herein can have the amino acid sequence set forth in SEQ ID NO:3 with a single F329M change. Other examples of BChE polypeptides provided herein are set forth in Table 1. In some cases, a BChE polypeptide provided herein can have an enhanced ability to hydrolyze acyl ghrelin as compared to a wild type human BChE having the amino acid sequence set forth in SEQ ID NO:3.

TABLE 1

Polypeptides based on human BChE.
Mutations with respect to SEQ ID NO: 3:

A199S, F227A, S287G, Y332Q and A328W
F329M
A199S, F227A, S287G, A328W, and F329M In some cases, a BChE polypeptide provided herein can have an enhanced ability to hydrolyze acyl ghrelin. For example, a nucleic acid vector can be designed to encode a BChE polypeptide that (a) contains one or more amino acid mutations with respect to a wild-type BChE polypeptide and (b) exhibits an elevated ability to hydrolyze acyl ghrelin with respect to the ability of that wild-type BChE polypeptide. In some cases, a nucleic acid vector can be designed to encode a BChE polypeptide that includes the amino acid sequence set forth in FIG. 1 or the amino acid sequence set forth in FIG. 1 with one or more (e.g., two, three, four, five, or six) of the following amino acid substitutions: A199S, S227A, S287G; A328W, F329M, or Y332G (amino acid numbering starts after the signal sequence). In some cases, such a BChE polypeptide can have an increased ability to hydrolyze acyl ghrelin as compared to a polypeptide having the amino acid sequence set forth in FIG. 1. In some cases, a nucleic acid vector can be designed to encode a BChE polypeptide that includes the amino acid sequence set forth in FIG. 2 or the amino acid sequence set forth in FIG. 2 with one or more (e.g., two, three, four, five, or six) of the following amino acid substitutions: A199S, F227A, S287G; A328W, F329M, or Y332G (amino acid numbering starts after the signal sequence). In some cases, such a BChE polypeptide can have an increased ability to hydrolyze acyl ghrelin as compared to a polypeptide having the amino acid sequence set forth in FIG. 2.

In some cases, a BChE polypeptide provided herein can have an amino acid sequence with at least 85% (e.g., 85%, 86%, 87%, 88%, 89%, 90%, 91%, 92%, 93%, 94%, 95%, 96%, 97%, 98%, 99%, or 100%) sequence identity to a reference sequence (e.g., SEQ ID NO:1 or 3). In some cases, a polypeptide provided herein can have an amino acid sequence with at least 85% (e.g., 85%, 86%, 87%, 88%, 89%, 90%, 91%, 92%, 93%, 94%, 95%, 96%, 97%, 98%, 99%, or 100%) sequence identity to SEQ ID NO:1 or 3, provided that the amino acid sequence is not identical to the sequence set forth in SEQ ID NO:1 and 3. Percent sequence identity is calculated by determining the number of matched positions in aligned amino acid sequences (target amino acid sequence aligned to an identified amino acid sequence), dividing the number of matched positions by the number of amino acids of the identified amino acid sequence (e.g., SEQ ID NO:3), and multiplying by 100. A matched position refers to a position in which identical amino acids occur at the same position in aligned amino acid sequences. Percent sequence identity also can be determined for any nucleic acid sequence.

Percent sequence identity is determined by comparing a target amino acid sequence to the identified amino acid sequence (e.g., SEQ ID NO:3) using the BLAST 2 Sequences (Bl2seq) program from the stand-alone version of BLASTZ containing BLASTN version 2.0.14 and BLASTP version 2.0.14. This stand-alone version of BLASTZ can be obtained on the World Wide Web from Fish & Richardson's web site (fr.com/blast) or the U.S. government's National Center for Biotechnology Information web site (ncbi.nlm.nih.gov). Instructions explaining how to use the Bl2seq program can be found in the readme file accompanying BLASTZ.

Bl2seq performs a comparison between two sequences using either the BLASTN or BLASTP algorithm. BLASTN is used to compare nucleic acid sequences, while BLASTP is used to compare amino acid sequences. To compare two nucleic acid sequences, the options are set as follows: -i is set to a file containing the first nucleic acid sequence to be compared (e.g., C:\seq1.txt); -j is set to a file containing the second nucleic acid sequence to be compared (e.g., C:\seq2.txt); -p is set to blastn; -o is set to any desired file name (e.g., C:\output.txt); -q is set to 1; -r is set to 2; and all other options are left at their default setting. The following command will generate an output file containing a comparison between two sequences: C:\Bl2-i seq c:\seq1.txt -j c:\seq2.txt -p blastn -o c:\output.txt -q -1 -r 2. If the target sequence shares homology with any portion of the identified sequence, then the designated output file will present those regions of homology as aligned sequences. If the target sequence does not share homology with any portion of the identified sequence, then the designated output file will not present aligned sequences.

For example, if (1) a target sequence is compared to the sequence set forth in a reference sequence that has 100 amino acid residues and (2) the Bl2seq program presents the target sequence aligned with a region of that sequence with the number of matches being 86, then the amino acid target sequence has a percent identity to that reference sequence that is 86 (i.e., 86÷100×100=86.0). It is noted that the percent identity value is rounded to the nearest tenth. For example, 78.11, 78.12, 78.13, and 78.14 are rounded down to 78.1, while 78.15, 78.16, 78.17, 78.18, and 78.19 are rounded up to 78.2. It also is noted that the length value will always be an integer.

A BChE polypeptide provided herein can be produced using any suitable method, including recombinant technology. In some cases, a polypeptide provided herein can be a substantially pure polypeptide. As used herein, the term "substantially pure" with reference to a polypeptide means that the polypeptide is substantially free of other polypeptides, lipids, carbohydrates, and nucleic acid. In some cases, a substantially pure polypeptide can be a polypeptide that is at least 60 percent pure or is any chemically synthesized polypeptide. A substantially pure polypeptide can be at least about 60, 65, 70, 75, 80, 85, 90, 95, or 99 percent pure. Typically, a substantially pure polypeptide will yield a single major band on a non-reducing polyacrylamide gel.

In some cases, a BChE polypeptide provided herein can be modified by linkage to a polymer such as polyethylene glycol (PEG), or by fusion to another polypeptide such as albumin, for example. For example, one or more PEG moieties can be conjugated to a polypeptide provided herein via lysine residues. Linkage to PEG or another suitable polymer, or fusion to albumin or another suitable polypeptide can result in a modified polypeptide having an increased half-life as compared to an unmodified polypeptide. Without being bound by a particular mechanism, an increased serum half-life can result from reduced proteolytic degradation, immune recognition, or cell scavanging of the modified polypeptide. Any appropriate method can be used to modify a polypeptide provided herein by linkage to PEG (also referred to as "PEGylation") or other polymers including, without limitation, those described elsewhere (U.S. Pat. No. 6,884,780; Cataliotti et al., *Trends Cardiovasc. Med.*, 17:10-14 (2007); Veronese and Mero, *BioDrugs*, 22:315-329 (2008); Miller et al., *Bioconjugate Chem.*, 17:267-274 (2006); and Veronese and Pasut, *Drug Discov. Today*, 10:1451-1458 (2005). Examples of methods for modifying a BChE polypeptide provided herein by fusion to albumin include, without limitation, those described elsewhere (U.S. Patent Publication No. 20040086976, and Wang et al., *Pharm. Res.*, 21:2105-2111 (2004)).

As used herein, the term "nucleic acid" refers to both RNA and DNA, including cDNA, genomic DNA, and synthetic (e.g., chemically synthesized) DNA. A nucleic acid molecule can be double-stranded or single-stranded (i.e., a sense or an antisense single strand). Nucleic acids include, for example, cDNAs encoding the chimeric polypeptides provided herein.

An "isolated nucleic acid" is a nucleic acid that is separated from other nucleic acid molecules that are present in a vertebrate genome, including nucleic acids that normally flank one or both sides of the nucleic acid in a vertebrate genome. The term "isolated" as used herein with respect to nucleic acids also includes any non-naturally-occurring nucleic acid sequence, since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule (e.g., a chemically synthesized nucleic acid, or a cDNA or genomic DNA fragment produced by PCR or restriction endonuclease treatment) independent of other sequences as well as DNA that is incorporated into a vector, an autonomously replicating plasmid, a virus (e.g., a retrovirus, lentivirus, adenovirus, or herpes virus), or into the genomic DNA of a prokaryote or eukaryote. In addition, an isolated nucleic acid can include an engineered nucleic acid such as a DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not considered an isolated nucleic acid.

Isolated nucleic acid molecules can be produced using standard techniques, including, without limitation, common molecular cloning and chemical nucleic acid synthesis techniques. For example, polymerase chain reaction (PCR) techniques can be used to obtain an isolated nucleic acid containing a nucleotide sequence that encodes a BChE polypeptide. PCR refers to a procedure or technique in which target nucleic acids are enzymatically amplified. Sequence information from the ends of the region of interest or beyond typically is employed to design oligonucleotide primers that are identical in sequence to opposite strands of the template to be amplified. PCR can be used to amplify specific sequences from DNA as well as RNA, including sequences from total genomic DNA or total cellular RNA. Primers typically are 14 to 40 nucleotides in length, but can range from 10 nucleotides to hundreds of nucleotides in length. General PCR techniques are described, for example in PCR Primer: A Laboratory Manual, ed. by Dieffenbach and Dveksler, Cold Spring Harbor Laboratory Press, 1995. When using RNA as a source of template, reverse transcriptase can be used to synthesize complementary DNA (cDNA) strands. Ligase chain reaction, strand displacement amplification, self-sustained sequence replication, or nucleic acid sequence-based amplification also can be used to obtain isolated nucleic acids. See, for example, Lewis, *Genetic Engineering News,* 12:1 (1992); Guatelli et al., *Proc. Natl. Acad. Sci. USA,* 87:1874-1878 (1990); and Weiss, *Science,* 254:1292 (1991)).

Isolated nucleic acids also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector.

Isolated nucleic acids (e.g., nucleic acids encoding a polypeptide provided herein) also can be obtained by mutagenesis. For example, a reference sequence (e.g., SEQ ID NO:2 or 4) can be mutated using standard techniques including oligonucleotide-directed mutagenesis and site-directed mutagenesis through PCR. See, Short Protocols in Molecular Biology, Chapter 8, Green Publishing Associates and John Wiley & Sons, edited by Ausubel et al., 1992.

As described herein, a nucleic acid vector can be designed to express a BChE polypeptide. Such nucleic acid vectors can include one or more expression control sequences. An "expression control sequence" is a nucleic acid sequence that controls and regulates the transcription and/or translation of another nucleic acid sequence.

In the expression vectors, a nucleic acid (e.g., a nucleic acid encoding a BChE polypeptide provided herein) can be operably linked to one or more expression control sequences. As used herein, "operably linked" means incorporated into a genetic construct so that expression control sequences effectively control expression of a coding sequence of interest. Examples of expression control sequences include promoters, enhancers, and transcription terminating regions. A promoter is an expression control sequence composed of a region of a DNA molecule, typically within 100 to 500 nucleotides upstream of the point at which transcription starts (generally near the initiation site for RNA polymerase II). To bring a coding sequence under the control of a promoter, it is necessary to position the translation initiation site of the translational reading frame of the polypeptide between one and about fifty nucleotides downstream of the promoter. Enhancers provide expression specificity in terms of time, location, and level. Unlike promoters, enhancers can function when located at various distances from the transcription site. An enhancer also can be located downstream from the transcription initiation site. A coding sequence is "operably linked" and "under the control" of expression control sequences in a cell when RNA polymerase is able to transcribe the coding sequence into mRNA, which then can be translated into the protein encoded by the coding sequence.

Suitable expression vectors include, without limitation, plasmids and viral vectors derived from, for example, bacteriophage, baculoviruses, tobacco mosaic virus, herpes viruses, cytomegalovirus, retroviruses, vaccinia viruses, adenoviruses, and adeno-associated viruses. In some cases, a viral vector can be virus particles such as type five adenovirus, helper-dependent adenovirus, adeno associated virus, measles virus, or lentivirus virus particles that are designed to express a wild type BChE polypeptide or mutant BChE polypeptide provided herein. In some cases, a viral vector such as an AAV8 viral vector, a lentiviral vector, or helper-dependent adenoviral vector can be designed to express a wild type BChE polypeptide or mutant BChE polypeptide provided herein. Numerous vectors and expression systems are commercially available from such corporations as Novagen (Madison, WI), Clontech (Palo Alto, CA), Stratagene (La Jolla, CA), and Invitrogen/Life Technologies (Carlsbad, CA).

An expression vector can include a tag sequence designed to facilitate subsequent manipulation of the expressed nucleic acid sequence (e.g., purification or localization). Tag sequences, such as green fluorescent protein (GFP), glutathione S-transferase (GST), polyhistidine, c-myc, hemagglutinin, or Flag™ tag (Kodak, New Haven, CT) sequences, typically are expressed as a fusion with the encoded polypeptide. Such tags can be inserted anywhere within the polypeptide including at either the carboxyl or amino terminus.

A wild type BChE polypeptide or mutant BChE polypeptide provided herein, or a nucleic acid encoding a wild type BChE polypeptide or mutant BChE polypeptide provided herein, can be incorporated into a composition for administration to a mammal having cancer (e.g., breast cancer or prostate cancer). For example, a viral vector designed to express a wild type BChE polypeptide or a mutant BChE polypeptide provided herein can be administered to a mammal (e.g., a human) having cancer under conditions wherein the number of cancer cells within the mammal and/or the growth rate of cancer cells within the mammal is reduced.

Compositions containing a wild type BChE polypeptide or mutant BChE polypeptide provided herein (or a nucleic acid vector encoding such a polypeptide) may be given once or more daily, weekly, monthly, or even less often, or can be administered continuously for a period of time (e.g., hours, days, or weeks). In some cases, preparations designed to stabilize a delivered BChE polypeptide may maintain effective activity in a mammal for several days.

In some cases, a nucleic acid vector (e.g., a viral vector) designed to express a wild type or mutant BChE polypeptide provided herein can be administered once to a mammal in a way that generates effective amounts of the BChE polypeptide for months or years (e.g., two years or longer). In some cases, such treatment can be extended by later administration of an equivalent viral vector of altered serotype (e.g., type 8 adenoviral vector) to express the same BChE polypeptide for extended treatments.

The BChE polypeptides provided herein (or nucleic acid vectors designed to express such BChE polypeptides) for treating cancer as described herein can be admixed, encapsulated, conjugated or otherwise associated with other molecules, molecular structures, or mixtures of compounds such as, for example, liposomes, receptor or cell targeted molecules, or oral, topical or other formulations for assisting in uptake, distribution and/or absorption. In some cases, a composition to be administered can contain a BChE polypeptide (or a nucleic acid vector designed to express a BChE polypeptide) in combination with a pharmaceutically acceptable carrier. Pharmaceutically acceptable carriers include, for example, pharmaceutically acceptable solvents, suspending agents, or any other pharmacologically inert vehicles for delivering polypeptides, nucleic acids, or viral vectors (e.g., viral particles) to a subject. Pharmaceutically acceptable carriers can be liquid or solid, and can be selected with the planned manner of administration in mind so as to provide for the desired bulk, consistency, and other pertinent transport and chemical properties, when combined with one or more therapeutic compounds and any other components of a given pharmaceutical composition. Typical pharmaceutically acceptable carriers include, without limitation: water; saline solution; binding agents (e.g., polyvinylpyrrolidone or hydroxypropyl methylcellulose); fillers (e.g., lactose or dextrose and other sugars, gelatin, or calcium sulfate); lubricants (e.g., starch, polyethylene glycol, or sodium acetate); disintegrates (e.g., starch or sodium starch glycolate); and wetting agents (e.g., sodium lauryl sulfate).

Acceptable solvents for delivery of viral vectors include, without limitation, common physiological salt solutions such as 0.9% sodium chloride, or isotonic aqueous solutions of sodium phosphate buffered to a pH of 7.4.

Pharmaceutical compositions containing a BChE polypeptide provided herein (or a nucleic acid vector designed to express a BChE polypeptide) can be administered by a number of methods including by subcutaneous, intrathecal, intraventricular, intramuscular, intraperitoneal, intratumoral, or intravenous injection.

The invention will be further described in the following example, which does not limit the scope of the invention described in the claims.

EXAMPLES

Example 1—Using Viral Vectors Expressing BChE Polypeptides to Treat Cancer

Viral Vectors

A serotype-8 adeno-associated viral vector (AAV-8) was generated to express the following polypeptides: 1) native mouse BChE; 2) mouse BChE lacking all catalytic activity because the active site peptide residue at position 198 was mutated from serine to alanine; and 3) luciferase, a functionally irrelevant protein. Then, to make AAV—VIP-BChE or AAV—VIP-Luc plasmids, each different version of BChE or Luciferase coding sequence was prepared by cloning into pAAVio-CASI vector (also called AAV-VIP), obtained from CalTech, which includes AAV2 ITRs, CMV enhancer, Chicken beta-actin promoter, and UBC Enhancer between Not I and BamH I endonucleases.

AAV8 Virus Production and Purification:

Recombinant AAV8 viral particles were generated by triple transfections including AAV-VIP-BChE or AAV-VIP-Luc plasmid, AAV2/8 and pHELPER of HEK293T using polyethylenimine (PEI). Viral particles were harvested from both the media and cell lysates at 96 hours post transfection. Cell pellets were resuspended in DPBS, freeze-thawed three times. Viral media were concentrated by precipitation with 8% polyethylene glycol 8000 (PEG8000, Sigma-Aldrich) and 0.5M sodium chloride, resuspended in DPBS. The clarified cell lysates and the media were combined and then purified over iodixanol (Optoprep, sigma; D1556) gradients of 15%, 25%, 40% and 54% by ultracentrifuge. Viruses were washed and concentrated with Ultracel-100K Centrifugal Filters (Merck Millipore, UFC910024) with DPBS. The virus titers were determined by measuring the number of DNase I resistant viral genome by qPCR with appropriate pAAV-VIP plasmid DNA as the reference standard.

Animal Models

Patient-derived tumor xenograft (PDX) models were generated as follows. Briefly, baseline pre-treatment percutaneous biopsy specimens were obtained sterile from newly diagnosed stage I to III breast cancer patients. These samples were received within one hour of the biopsy and were implanted subcutaneously in 6 to 8 week-old female NOD-SCID (NOD.CB17-Prkdc$^{scid}$/J) or NSG (NOD.Cg-Prkdc$^{scid}$ Il2rg$^{tm1Wjl}$/SzJ) mice which were maintained and pretreated with 17β-Estradiol.

A Triple Negative PDX tumor was expanded subcutaneously to 30 mice. When tumors grew to 100-200 mm$^3$, mice were randomized to different treatment groups with each group having 6-7 mice. $10^{13}$ viral particles of control vectors or BChE vectors were injected into the tail vein. In another group of mice, BChE vectors were injected into both the tail vein and the implanted tumor mass. Tumor volume was measured using digital calipers every week. Tumor volumes were calculated using the formula ½×L×W$^2$.

Results

Two-way analysis of variance indicated a highly significant difference between controls and both experimental groups (FIG. 3; p<0.001). There was no difference between the two treated groups up to the 10-week sampling point, but the data revealed that systemic tail vein injection alone was as effective against tumor growth as was the double treatment that included an intra-tumor injection (FIG. 3).

Along with measures of tumor volume, mouse blood samples were collected at intervals to determine circulating levels of transduced BChE, using a spectrometric Ellman method described elsewhere (Garry, Clin. Chem., 17:183-91 (1971)) and separately to measure ghrelin levels by ELISA as described elsewhere (Chen et al., Proc. Natl. Acad. Sci. USA, 112:2251-2256 (2015)). The elevation of circulating BChE polypeptides was close to 30-fold. Measures of desacyl ghrelin, the hormone breakdown product, revealed that BChE treatment caused a 2-fold rise in the ratio of inactive peptide over the active hormone. Although the effect on ghrelin appeared to be modest, tumor growth was substantially suppressed.

These results demonstrate that nucleic acid vectors designed to express BChE polypeptides can be used to inhibit tumor growth.

Example 2—Viral Vectors for Treating Humans with Cancer

An AAV-8 viral vector is designed to express a human BChE polypeptide. This AAV-8 viral vector is administered to a human having cancer to treat the cancer within the human. The treated human is monitored for levels of enzyme activity and levels of ghrelin in the blood stream before and after treatment is given. Optionally, vector treatment is given when the patient is receiving traditional chemotherapy at the same time.

Example 3—Using Viral Vectors Expressing BChE Polypeptides to Treat Colorectal Cancer AAV vectors carrying BChE or Luciferase (Luc) gene were delivered via tail vein into 6 weeks old Female Athymic nu/nu mice. Briefly, ten female athymic, immunocompromised nu/nu mice were used to test the impact of BChE gene transfer. They received 10$^3$ units (viral particles)

of BChE- or Luciferase-expressing AAV viral vector delivered via the tail vein under general anesthesia at 6 to 8 weeks of age. Seven days after the injections, BChE and Ghrelin levels in the blood stream were monitored. At this time, $1 \times 10^6$ logarithmically HCT116 colon cancer cells growing in petri dishes were mixed 1:1 with Matrigel, and injected subcutaneously into the mice over the sacroiliac joint in a volume of 100 µL through an 18 g needle. Tumor growth was monitored on a daily basis by measuring tumor length (L) and width (W) using a caliper. Tumor volume (TV) was calculated using the formula: $TV=(L \times W^2)/2$. Each animal was followed until animals in the "unprotected" luciferase control group reached an extreme tumor burden or weight loss of more than 20%. At this point, all mice were euthanized by narcosis with $CO^2$.

Figure 4:
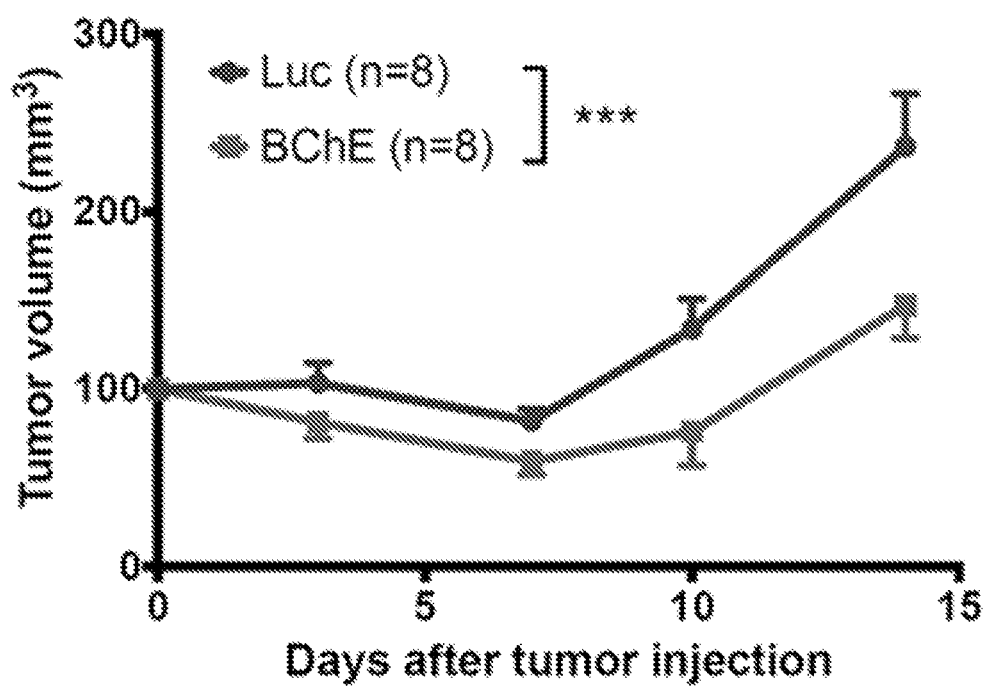
FIG. 4 is a graph plotting colorectal tumor growth after BChE gene transfer. Six-week old female Athymic nu/nu mice were i.v. injected with AAV-Luc or AAV-BChE at the dose of $10^{13}$ viral particles per mouse. Three weeks after viral injection, all mice were implanted with $10^6$ logarithmically growing HCT116 colon cancer cells under the skin overlying sacroiliac joint. Tumor sizes were monitored at the indicated time points.

Two-way analysis of variance indicated a highly significant difference between control and treatment groups (FIG. 4; $p<0.001$). There was no difference between the treatment group up to the 10-week sampling point, but the data revealed that systemic tail vein injection was as effective against tumor growth (FIG. 4).

Along with measures of tumor volume, mouse blood samples were collected at intervals to determine circulating levels of transduced BChE, using a spectrometric Ellman method described elsewhere (Garry, *Clin. Chem.*, 17:183-91 (1971)) and separately to measure ghrelin levels by ELISA as described elsewhere (Chen et al., *Proc. Natl. Acad. Sci. USA*, 112:2251-2256 (2015)). The elevation of circulating BChE polypeptides was close to 30-fold. Measures of desacyl ghrelin, the hormone breakdown product, revealed that BChE treatment caused a 2-fold rise in the ratio of inactive peptide over the active hormone. Although the effect on ghrelin appeared to be modest, tumor growth was substantially suppressed.

These results demonstrate that nucleic acid vectors designed to express BChE polypeptides can be used to inhibit colon cancer growth (e.g., colorectal cancer growth).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating triple negative breast cancer within a mammal, wherein said method comprises administering a butyrylcholinesterase (BChE) polypeptide or a nucleic acid encoding said polypeptide to said mammal, wherein the number of cancer cells within said mammal is reduced or the growth rate of said cancer within said mammal is reduced, and wherein said BChE polypeptide is not modified by fusion to another polypeptide.

2. The method of claim 1, wherein said mammal is a human.

3. The method of claim 1, wherein said method comprises administering said BChE polypeptide to said mammal.

4. The method of claim 1, wherein said method comprises administering said nucleic acid to said mammal.

5. The method of claim 4, wherein said nucleic acid is administered to said mammal as a viral vector.

6. The method of claim 5, wherein said viral vector is an adenoviral or adeno-associated viral vector.

7. The method of claim 1, wherein said BChE polypeptide is a human BChE polypeptide.

8. The method of claim 1, wherein said BChE polypeptide comprises the amino acid sequence set forth in SEQ ID NO:3.

9. The method of claim 1, wherein said BChE polypeptide comprises the amino acid sequence set forth in SEQ ID NO:3 with a F329M substitution or with a combination with one or more of the following amino acid substitutions: A199S, F227A, S287G, A328W, F329M, or Y332G wherein the amino acid numbering of A199S, F227A, S287G, A328W, F329M, and Y332G starts after the signal sequence of SEQ ID NO:3.

10. The method of claim 1, wherein said BChE polypeptide consists of the amino acid sequence set forth in SEQ ID NO:3.

11. The method of claim 1, wherein said BChE polypeptide consists of the amino acid sequence set forth in SEQ ID NO:3 with a F329M substitution or with a combination with one or more of the following amino acid substitutions: A199S, F227A, S287G, A328W, F329M, or Y332G wherein the amino acid numbering of A199S, F227A, S287G, A328W, F329M, and Y332G starts after the signal sequence of SEQ ID NO:3.

* * * * *

SEQUENCE LISTING

```
<160> NUMBER OF SEQ ID NOS: 4

<210> SEQ ID NO 1
<211> LENGTH: 603
<212> TYPE: PRT
<213> ORGANISM: Mus musculus

<400> SEQUENCE: 1

Met Glu Thr Gln His Thr Lys Val Thr Gln Thr His Phe Leu Leu Trp
1               5                   10                  15

Ile Leu Leu Leu Cys Met Pro Phe Gly Lys Ser His Thr Glu Glu Asp
            20                  25                  30

Phe Ile Ile Thr Thr Lys Thr Gly Arg Val Arg Gly Leu Ser Met Pro
        35                  40                  45

Val Leu Gly Gly Thr Val Thr Ala Phe Leu Gly Ile Pro Tyr Ala Gln
    50                  55                  60

Pro Pro Leu Gly Ser Leu Arg Phe Lys Lys Pro Gln Pro Leu Asn Lys
65                  70                  75                  80

Trp Pro Asp Ile His Asn Ala Thr Gln Tyr Ala Asn Ser Cys Tyr Gln
                85                  90                  95

Asn Ile Asp Gln Ala Phe Pro Gly Phe Gln Gly Ser Glu Met Trp Asn
            100                 105                 110

Pro Asn Thr Asn Leu Ser Glu Asp Cys Leu Tyr Leu Asn Val Trp Ile
        115                 120                 125

Pro Val Pro Lys Pro Lys Asn Ala Thr Val Met Val Trp Ile Tyr Gly
    130                 135                 140

Gly Gly Phe Gln Thr Gly Thr Ser Ser Leu Pro Val Tyr Asp Gly Lys
145                 150                 155                 160

Phe Leu Ala Arg Val Glu Arg Val Ile Val Val Ser Met Asn Tyr Arg
                165                 170                 175

Val Gly Ala Leu Gly Phe Leu Ala Phe Pro Gly Asn Pro Asp Ala Pro
            180                 185                 190

Gly Asn Met Gly Leu Phe Asp Gln Gln Leu Ala Leu Gln Trp Val Gln
        195                 200                 205
```

```
Arg Asn Ile Ala Ala Phe Gly Gly Asn Pro Lys Ser Ile Thr Ile Phe
    210                 215                 220
Gly Glu Ser Ala Gly Ala Ser Val Ser Leu His Leu Leu Cys Pro
225                 230                 235                 240
Gln Ser Tyr Pro Leu Phe Thr Arg Ala Ile Leu Glu Ser Gly Ser Ser
                245                 250                 255
Asn Ala Pro Trp Ala Val Lys His Pro Glu Glu Ala Arg Asn Arg Thr
            260                 265                 270
Leu Thr Leu Ala Lys Phe Thr Gly Cys Ser Lys Glu Asn Glu Met Glu
        275                 280                 285
Met Ile Lys Cys Leu Arg Ser Lys Asp Pro Gln Glu Ile Leu Arg Asn
290                 295                 300
Glu Arg Phe Val Leu Pro Ser Asp Ser Ile Leu Ser Ile Asn Phe Gly
305                 310                 315                 320
Pro Thr Val Asp Gly Asp Phe Leu Thr Asp Met Pro His Thr Leu Leu
                325                 330                 335
Gln Leu Gly Lys Val Lys Lys Ala Gln Ile Leu Val Gly Val Asn Lys
            340                 345                 350
Asp Glu Gly Thr Ala Phe Leu Val Tyr Gly Ala Pro Gly Phe Ser Lys
        355                 360                 365
Asp Asn Asp Ser Leu Ile Thr Arg Lys Glu Phe Gln Glu Gly Leu Asn
370                 375                 380
Met Tyr Phe Pro Gly Val Ser Arg Leu Gly Lys Glu Ala Val Leu Phe
385                 390                 395                 400
Tyr Tyr Val Asp Trp Leu Gly Glu Gln Ser Pro Glu Val Tyr Arg Asp
                405                 410                 415
Ala Leu Asp Asp Val Ile Gly Asp Tyr Asn Ile Ile Cys Pro Ala Leu
            420                 425                 430
Glu Phe Thr Lys Lys Phe Ala Glu Leu Glu Asn Asn Ala Phe Phe Tyr
        435                 440                 445
Phe Phe Glu His Arg Ser Ser Lys Leu Pro Trp Pro Glu Trp Met Gly
450                 455                 460
Val Met His Gly Tyr Glu Ile Glu Phe Val Phe Gly Leu Pro Leu Gly
465                 470                 475                 480
Arg Arg Val Asn Tyr Thr Arg Ala Glu Glu Ile Phe Ser Arg Ser Ile
                485                 490                 495
Met Lys Thr Trp Ala Asn Phe Ala Lys Tyr Gly His Pro Asn Gly Thr
            500                 505                 510
Gln Gly Asn Ser Thr Met Trp Pro Val Phe Thr Ser Thr Glu Gln Lys
        515                 520                 525
Tyr Leu Thr Leu Asn Thr Glu Lys Ser Lys Ile Tyr Ser Lys Leu Arg
530                 535                 540
Ala Pro Gln Cys Gln Phe Trp Arg Leu Phe Phe Pro Lys Val Leu Glu
545                 550                 555                 560
Met Thr Gly Asp Ile Asp Glu Thr Glu Gln Glu Trp Lys Ala Gly Phe
                565                 570                 575
His Arg Trp Ser Asn Tyr Met Met Asp Trp Gln Asn Gln Phe Asn Asp
            580                 585                 590
Tyr Thr Ser Lys Lys Glu Ser Cys Thr Ala Leu
        595                 600

<210> SEQ ID NO 2
<211> LENGTH: 1812
```

<212> TYPE: DNA
<213> ORGANISM: Mus musculus

<400> SEQUENCE: 2

```
atggagactc agcataccaa ggtaacacag acccacttcc tcctatggat tcttctgctc      60
tgcatgcctt ttgggaagtc acacactgaa aagacttca taattacaac caagaccgga     120
agggtccgag ggctgagcat gccagttctt ggtggcacgg tgactgcctt tctcggtatc     180
ccctatgcac aacctcctct gggtagccta agattcaaaa agccgcaacc cttaaacaaa     240
tggcctgaca tccataatgc cactcaatat gcaaattctt gttatcagaa catagaccaa     300
gccttcccag gcttccaggg gtcagaaatg tggaatccaa acacaaacct cagtgaagac     360
tgcttgtatc tgaatgtttg gattccagta ccgaagccta aaaatgccac tgtcatggta     420
tggatctatg gtggtggctt tcaaactggg acctcttctc tacctgttta cgatgggaag     480
tttctagctc gtgttgaaag agttattgta gtttcgatga actatagggt aggtgctcta     540
ggattcctag cttttcccgg aaatcccgat gctccaggaa acatgggttt atttgatcaa     600
cagttggcac ttcaatgggt ccaaagaaat atagctgctt ttggagggaa tcctaaaagt     660
ataacgattt ttggagaaag tgcaggggca gcttcagtta gcttacattt gctctgcccc     720
caaagttatc ctttgtttac cagagccatt cttgaaagtg gctcctctaa tgcccctgg     780
gcagtaaagc atcctgagga agccagaaac agaaccttga ccttagctaa atttactggt     840
tgctcaaagg aaaatgagat ggagatgatt aaatgccttc gaagtaaaga tcctcaggaa     900
attcttcgca tgaaaggtt cgttctcccc tctgattcca tcttatccat aaatttttggt     960
ccaacagtgg atggcgattt tctcaccgat atgccccaca cactactcca actaggaaaa    1020
gtgaaaaaag ctcagatctt agtgggagtt aacaaagatg aagggacagc tttcctagtg    1080
tacggtgctc cgggtttcag caaagacaat gatagcctta tcacaaggaa ggaatttcaa    1140
gaaggtttaa atatgtattt ccctggagtg agcagattgg gcaaggaagc agttcttttc    1200
tactacgtgg actggttagg tgagcagtca ccagaagtct accgtgacgc tttggatgat    1260
gttattggag attacaacat catctgccct gcactggagt ttaccaagaa atttgcagag    1320
cttgaaaaca atgctttttt ctactttttc gaacatcgct cttccaaact accttggccg    1380
gaatggatgg gagtgatgca tggctatgaa attgaatttg tgtttggctt acctctggga    1440
agaagagtta attatacgag agctgaggaa atctttagtc gatccataat gaaaacttgg    1500
gcaaattttg caaaatatgg tcaccccaat gggacccagg gcaatagcac aatgtggcct    1560
gtcttcacaa gtactgaaca aaaataccta acattgaaca cagagaagtc aaaaatatac    1620
tctaaacttc gtgctcccca atgtcagttc tggagactat tttttccaaa agtcttggaa    1680
atgacaggag atattgatga acggagcaa gagtggaagg caggatttca tcgctggagc    1740
aattacatga tggactggca aaatcaattt aacgattaca ctagcaagaa agagagctgt    1800
acagctctct aa                                                        1812
```

<210> SEQ ID NO 3
<211> LENGTH: 602
<212> TYPE: PRT
<213> ORGANISM: Homo sapiens

<400> SEQUENCE: 3

```
Met His Ser Lys Val Thr Ile Ile Cys Ile Arg Phe Leu Phe Trp Phe
 1               5                   10                  15

Leu Leu Leu Cys Met Leu Ile Gly Lys Ser His Thr Glu Asp Asp Ile
```

```
            20                  25                  30
Ile Ile Ala Thr Lys Asn Gly Lys Val Arg Gly Met Asn Leu Thr Val
        35                  40                  45
Phe Gly Gly Thr Val Thr Ala Phe Leu Gly Ile Pro Tyr Ala Gln Pro
    50                  55                  60
Pro Leu Gly Arg Leu Arg Phe Lys Lys Pro Gln Ser Leu Thr Lys Trp
65                  70                  75                  80
Ser Asp Ile Trp Asn Ala Thr Lys Tyr Ala Asn Ser Cys Cys Gln Asn
                85                  90                  95
Ile Asp Gln Ser Phe Pro Gly Phe His Gly Ser Glu Met Trp Asn Pro
            100                 105                 110
Asn Thr Asp Leu Ser Glu Asp Cys Leu Tyr Leu Asn Val Trp Ile Pro
        115                 120                 125
Ala Pro Lys Pro Lys Asn Ala Thr Val Leu Ile Trp Ile Tyr Gly Gly
        130                 135                 140
Gly Phe Gln Thr Gly Thr Ser Ser Leu His Val Tyr Asp Gly Lys Phe
145                 150                 155                 160
Leu Ala Arg Val Glu Arg Val Ile Val Val Ser Met Asn Tyr Arg Val
                165                 170                 175
Gly Ala Leu Gly Phe Leu Ala Leu Pro Gly Asn Pro Glu Ala Pro Gly
            180                 185                 190
Asn Met Gly Leu Phe Asp Gln Gln Leu Ala Leu Gln Trp Val Gln Lys
        195                 200                 205
Asn Ile Ala Ala Phe Gly Gly Asn Pro Lys Ser Val Thr Leu Phe Gly
        210                 215                 220
Glu Ser Ala Gly Ala Ala Ser Val Ser Leu His Leu Leu Ser Pro Gly
225                 230                 235                 240
Ser His Ser Leu Phe Thr Arg Ala Ile Leu Gln Ser Gly Ser Phe Asn
                245                 250                 255
Ala Pro Trp Ala Val Thr Ser Leu Tyr Glu Ala Arg Asn Arg Thr Leu
            260                 265                 270
Asn Leu Ala Lys Leu Thr Gly Cys Ser Arg Glu Asn Glu Thr Glu Ile
        275                 280                 285
Ile Lys Cys Leu Arg Asn Lys Asp Pro Gln Glu Ile Leu Leu Asn Glu
        290                 295                 300
Ala Phe Val Val Pro Tyr Gly Thr Pro Leu Ser Val Asn Phe Gly Pro
305                 310                 315                 320
Thr Val Asp Gly Asp Phe Leu Thr Asp Met Pro Asp Ile Leu Leu Glu
                325                 330                 335
Leu Gly Gln Phe Lys Lys Thr Gln Ile Leu Val Gly Val Asn Lys Asp
            340                 345                 350
Glu Gly Thr Ala Phe Leu Val Tyr Gly Ala Pro Gly Phe Ser Lys Asp
        355                 360                 365
Asn Asn Ser Ile Ile Thr Arg Lys Glu Phe Gln Glu Gly Leu Lys Ile
        370                 375                 380
Phe Phe Pro Gly Val Ser Glu Phe Gly Lys Glu Ser Ile Leu Phe His
385                 390                 395                 400
Tyr Thr Asp Trp Val Asp Asp Gln Arg Pro Glu Asn Tyr Arg Glu Ala
                405                 410                 415
Leu Gly Asp Val Val Gly Asp Tyr Asn Phe Ile Cys Pro Ala Leu Glu
            420                 425                 430
Phe Thr Lys Lys Phe Ser Glu Trp Gly Asn Asn Ala Phe Phe Tyr Tyr
        435                 440                 445
```

```
Phe Glu His Arg Ser Ser Lys Leu Pro Trp Pro Glu Trp Met Gly Val
        450                 455                 460
Met His Gly Tyr Glu Ile Glu Phe Val Phe Gly Leu Pro Leu Glu Arg
465                 470                 475                 480
Arg Asp Asn Tyr Thr Lys Ala Glu Glu Ile Leu Ser Arg Ser Ile Val
                485                 490                 495
Lys Arg Trp Ala Asn Phe Ala Lys Tyr Gly Asn Pro Asn Glu Thr Gln
            500                 505                 510
Asn Asn Ser Thr Ser Trp Pro Val Phe Lys Ser Thr Glu Gln Lys Tyr
        515                 520                 525
Leu Thr Leu Asn Thr Glu Ser Thr Arg Ile Met Thr Lys Leu Arg Ala
    530                 535                 540
Gln Gln Cys Arg Phe Trp Thr Ser Phe Phe Pro Lys Val Leu Glu Met
545                 550                 555                 560
Thr Gly Asn Ile Asp Glu Ala Glu Trp Glu Trp Lys Ala Gly Phe His
                565                 570                 575
Arg Trp Asn Asn Tyr Met Met Asp Trp Lys Asn Gln Phe Asn Asp Tyr
            580                 585                 590
Thr Ser Lys Lys Glu Ser Cys Val Gly Leu
        595                 600

<210> SEQ ID NO 4
<211> LENGTH: 1809
<212> TYPE: DNA
<213> ORGANISM: Homo sapiens

<400> SEQUENCE: 4
atgcatagca aagtcacaat catatgcatc agatttctct tttggtttct tttgctctgc    60
atgcttattg ggaagtcaca tactgaagat gacatcataa ttgcaacaaa gaatggaaaa   120
gtcagaggga tgaacttgac agttttggt ggcacggtaa cagcctttct tggaattccc    180
tatgcacagc cacctcttgg tagacttcga ttcaaaaagc cacagtctct gaccaagtgg   240
tctgatattt ggaatgccac aaaatatgca aattcttgct gtcagaacat agatcaaagt   300
tttccaggct ccatggatc agagatgtgg aacccaaaca ctgacctcag tgaagactgt    360
ttatatctaa atgtatggat ccagcacct aaaccaaaaa atgccactgt attgatatgg    420
atttatggtg gtggttttca aactggaaca tcatctttac atgtttatga tggcaagttt   480
ctggctcggg ttgaaagagt tattgtagtg tcaatgaact atagggtggg tgccctagga   540
ttcttagctt gccaggaaa tcctgaggct ccagggaaca tgggtttatt tgatcaacag    600
ttggctcttc agtgggttca aaaaaatata gcagcctttg gtggaaatcc taaaagtgta   660
actctctttg gagaaagtgc aggagcagct tcagttagcc tgcatttgct ttctcctgga   720
agccattcat tgttcaccag agccattctg caaagtggat cctttaatgc ccttgggcg    780 gtaacatctc tttatgaagc taggaacaga acgttgaact tagctaaatt gactggttgc   840
tctagagaga atgagactga ataatcaag tgtcttagaa ataaagatcc ccaagaaatt    900
cttctgaatg aagcatttgt tgtccccta gggactcctt tgtcagtaaa ctttggtccg    960
accgtggatg tgatttttct cactgacatg ccagacatat acttgaact tggacaattt   1020 aaaaaaaccc agattttggt gggtgttaat aaagatgaag ggacagcttt tttagtctat   1080
ggtgctcctg gcttcagcaa agataacaat agtatcataa ctagaaaaga atttcaggaa   1140
ggtttaaaaa tattttttcc aggagtgagt gagtttggaa aggaatccat ccttttcat   1200
```

-continued

```
tacacagact gggtagatga tcagagacct gaaaactacc gtgaggcctt gggtgatgtt    1260
gttggggatt ataatttcat atgccctgcc ttggagttca ccaagaagtt ctcagaatgg    1320
ggaaataatg ccttttctcta ctattttgaa caccgatcct ccaaacttcc gtggccagaa   1380
tggatgggag tgatgcatgg ctatgaaatt gaatttgtct ttggtttacc tctggaaaga   1440
agagataatt acacaaaagc cgaggaaatt ttgagtagat ccatagtgaa acggtgggca   1500
aattttgcaa aatatgggaa tccaaatgag actcagaaca atagcacaag ctggcctgtc   1560
ttcaaaagca ctgaacaaaa atatctaacc ttgaatacag agtcaacaag aataatgacg   1620
aaactacgtg ctcaacaatg tcgattctgg acatcatttt ttccaaaagt cttggaaatg   1680
acaggaaata ttgatgaagc agaatgggag tggaaagcag gattccatcg ctggaacaat   1740
tacatgatgg actggaaaaa tcaatttaac gattacacta gcaagaaaga aagttgtgtg   1800
ggtctctaa                                                            1809
```